United States Patent [19]

Ennis et al.

[11] Patent Number: 5,302,599
[45] Date of Patent: Apr. 12, 1994

[54] THERAPEUTICALLY USEFUL HETEROCYCLIC INDOLE COMPOUNDS

[75] Inventors: Michael D. Ennis, Portage, Mich.; Mark E. Baze, Los Altos, Calif.

[73] Assignee: The Upjohn Company, Kalamazoo, Mich.

[21] Appl. No.: 945,323

[22] Filed: Sep. 15, 1992

Related U.S. Application Data

[63] Continuation of Ser. No. 494,100, Mar. 15, 1990, abandoned.

[51] Int. Cl.$^5$ ............... A61K 31/44; A61K 31/445; A61K 31/40; C07D 471/10; C07D 211/68; C07D 491/00

[52] U.S. Cl. ............... 514/278; 514/321; 514/322; 514/411; 546/20; 546/193; 546/194; 546/197; 546/199; 548/430; 548/431

[58] Field of Search ............... 546/20, 193, 194, 197, 546/199; 548/430, 431; 514/278, 321, 411, 322

[56] References Cited

U.S. PATENT DOCUMENTS

| | | | |
|---|---|---|---|
| 4,370,341 | 1/1983 | Asselin et al. | 424/274 |
| 4,454,150 | 6/1984 | Asselin et al. | 424/274 |
| 4,510,157 | 4/1985 | Asselin et al. | 514/411 |

FOREIGN PATENT DOCUMENTS

109039  5/1984  European Pat. Off. ............... 221/10

OTHER PUBLICATIONS

Partsvaniya, D. A. et al., "Synthesis and pharmacological activity of 5,6- and 4,5-ethylendioxytryptamines," Khim.-Farm. Zh. 20(12) 1454-9 (Russ.) [1986]; CA 106(23):196345r.
Derwent Abstract of EP153083 (Feb. 6, 1984).
Derwent Abstract of EP23761 (Jul. 2, 1899).
Derwent Abstract of BE827282 (Mar. 28, 1974).
Derwent Abstract of BE827283 (Mar. 28, 1974).
Derwent Abstract of BE827284 (Mar. 28, 1974).
Derwent Abstract of BE827285 (Mar. 28, 1974).
Derwent Abstract of BE827286 (Mar. 28, 1974).
Derwent Abstract of BE827287 (Mar. 28, 1974).
Ennis et al., J. Med. Chem. 35(16) 3058-66 (1992).
Ennis et al., Chem. Abst. 115(25):279812c (1991).

*Primary Examiner*—Cecilia Tsang
*Attorney, Agent, or Firm*—Donald L. Corneglio

[57] ABSTRACT

A therapeutically useful compound of formula I

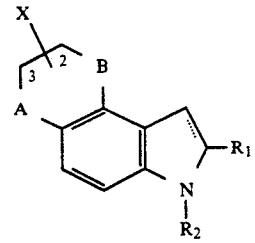

or pharmaceutically acceptable salts thereof where A and B are oxygen, sulfur or $CH_2$, X is an amine moiety as defined herein and $R_1$ and $R_2$ are as defined herein having $5HT_{1A}$ neuronal activity and/or dopamine receptor activity useful in the treatment of central nervous system and cardiovascular system disorders.

8 Claims, No Drawings

THERAPEUTICALLY USEFUL HETEROCYCLIC INDOLE COMPOUNDS

CROSS-REFERENCE TO RELATED APPLICATIONS

This application is a continuation of PCT/US91/00117, filed Jan. 15, 1991, WO 9113872, published Sep. 19, 1991 which was a continuation of U.S. Ser. No. 07/494,100, filed Mar. 15, 1990, abandoned.

BACKGROUND OF THE INVENTION

The present invention is related to new heterocyclic compounds containing both an indole and a 1,4-dioxan portion, processes for preparing such compounds, pharmaceutical preparation of such compounds and the use of such compounds in manufacture of a pharmaceutical preparation.

Psychiatric diseases are thought to be due to dysfunctions in monoaminergic neuronal systems, particularly those involving serotonin (5-HT) and dopamine (DA).

Anxiety is associated with increased activity in 5-HT systems. In animals where 5-HT has been depleted, benzodiazepine anxiolytics are not active in anti-anxiety assays that they otherwise are effective in. Seronotin neurons have autoreceptors that, when activated by agonists, depress firing rates of 5-HT cells. These receptors are of the 5-HT1A subtype. Because they depress 5-HT neuronal activity, it can be expected that 5-HT1A agonists will be anxiolytic.

Depression is a psychiatric condition thought to be associated with decreased 5-HT release. Most antidepressants potentiate the effects of 5-HT by blocking the termination of activity through reuptake into nerve terminals. Since some 5-HT1A receptors are activated postsynaptically by 5-HT, 5HT1A agonists may also be anti-depressants. Since the postsynaptic 5-HT1A receptor may be less sensitive than the autoreceptor, high doses of 5-HT1A agonists, particularly very effective ones (i.e., those causing greater stimulation of the 5-HT1A receptor, a parameter referred to as "efficacy"), can be expected to be effective anti-depressants.

5-HT1A agonists are known to depress sympathetic nerve discharge and thus lower blood pressure. Thus, they may be useful in treating hypertension, congestive heart failure (by reducing cardiovascular afterload) and heart attack (be removing sympathetic drive to the heart). 5-HT1A agonists may also be useful in treating overeating and sexual dysfunction. These compounds have been shown to alter feeding and sexual behavior in animals.

Schizophrenia is thought to be due to hyperactivity in DA systems. Thus, currently available anti-psychotics are DA antagonists. Dopamine autoreceptors depress DA neuron firing rates, DA synthesis and release. Thus DA autoreceptor agonists can also be expected to be anti-psychotics. DA agonists are also useful for treating Parkinsonism, a disease caused by degeneration of DA neurons, and hyperprolactinemia, since DA agonists depress prolactin release.

Dopamine autoreceptor antagonists are a new class of drug that increase release of DA by releasing the DA neuron from autoreceptor control. Thus, these drugs can be expected to be useful in conditions treatable with amphetamine and other similar stimulants which directly release DA. However, DA autoreceptor agonists will be much milder stimulants because, rather than directly releasing DA, they simply increase the release associated with the normal DA activity by releasing the cell from autoreceptor control. Thus, DA autoreceptor antagonists can be expected to be useful in treating overeating, attention deficit disorders, psychiatric, cognitive and motor retardation in demented and elderly patients, and in treating nausea and dizziness with space travel.

The compounds of the present invention have a variety of effects at 5-HT1A and DA receptors, and offer a variety of utilities associated with those activities.

Clinically, 5-HT1A agonists have also demonstrated anxiolytic properties. These compounds antagonize dopamine receptors at the same dose they stimulate 5-HT1A receptors.

The search for new CNS active compounds is focused on finding compounds with selective 5-HT1A receptor agonist effects without detrimentally influencing central dopamine receptors.

Drugs acting on central dopamine transmission are clinically effective in treating a variety of central nervous system disorders such as parkinsonism, schizophrenia, and mano-depressive illness. In parkinsonism, for example, the nigro-neostriatal hypofunction can be restored by an increase in postsynaptic dopamine receptor stimulation. In schizophrenia, the condition can be normalized by achieving a decrease in postsynaptic dopamine receptor stimulation. Classical and-psychotic agents directly block the postsynaptic dopamine receptor. The same effect can be achieved by inhibition of intraneuronal presynaptic events essential for the maintenance of adequate neurotransmission, transport mechanism and transmitter synthesis.

In recent years a large body of pharmacological, biochemical and electrophysical evidence has provided considerable support in favor of the existence of a specific population of central autoregulatory dopamine receptors located in the dopaminergic neuron itself These receptors are part of a homeostatic mechanism that modulates nerve impulse flow and transmitter synthesis and regulates the amount of dopamine released from the nerve endings.

Direct dopamine receptor agonists, like apomorphine, are able to activate the dopamine autoreceptors as well as the post synaptic dopamine receptors. The effects of autoreceptor stimulation appear to predominate when apomorphine is administered at low doses, whereas at higher doses the attenuation of dopamine transmission is outweighed by the enhancement of postsynaptic receptor stimulation. The anti-psychotic and anti-dyskinetic effects in man of low doses of apomorphine are likely due to the autoreceptor-stimulator properties of this dopamine receptor agonist. This body of knowledge indicates dopamine receptor stimulants with a high selectivity for central nervous dopamine autoreceptors would be valuable in treating psychiatric disorders.

INFORMATION DISCLOSURE STATEMENT

A tricyclic benzoquinoline compound has been described in EP 109 039 A by Yoshitomi Pharmaceutical Ind. KK which alleges antihypertensive activity.

A tricyclic indole containing compound is described in Chemical Abstract (CA 106(23):196345 entitled "Synthesis and pharmacological activity of 5,6- and 4,5-ethylendioxytryptamines; however, the structure lacks substitution on the dioxan ring and includes additional substitution on the indole.

U.S. Pat. Nos. 4,370,341 and 4,454,150 disclose 6,7,8,9-tetrahydro-3H-benz(e)indoleamines having dopamine-receptor stimulating activity; however, they structurally differ in that the instant compound has a badging alkylene between the benzene ring and amine.

U.S. Pat. No. 4,510,157 describes another tricyclic structure containing an indole ring useful as dodpamine receptors, however, not with the same structural orientation.

Other heterocyclic dopamine receptors or alleged antidepressants having differently fused rings or structural arrangement are reported in EP 153 083 A by Eli Lilly & Co.; EP 23 761 by Smith Kline Corp; and a group of published applications by Marion Labs BE 827282-287.

SUMMARY OF THE INVENTION

The present invention is directed toward therapeutically useful compounds having the structural Formula 1, as shown on the formula sheets below, or pharmaceutically acceptable salts thereof Wherein, $R_1$ is hydrogen, $C_1$-$C_6$ alkyl, $C_2$-$C_8$ alkenyl, $C_2$-$C_8$ alkynyl, —$CO_2R_2$, —$CONHR_2$, —CN, halogen, —CHO, —$(CH_2)_m$—$OR_2$, —$(CH_2)_m$—Ar, or —$SO_2R_2$;

$R_2$ is hydrogen, $C_1$-$C_6$ alkyl, $C_2$-$C_8$ alkenyl, $C_2$-$C_8$ alkynyl, —$(CH_2)_m$($C_3$-$C_8$) cycloalkyl or cycloalkenyl, or —$(CH_2)_m$—Ar where Ar is phenyl, pyridyl, naphthyl, indolyl optionally substituted with one or more of the following: —$OR_2$, halogen, —CN, —CHO, —$(CH_2)_m$—Ph, —$NO_2$, —$SR_2$ or $NHR_2$ and m is 0 to 6;

A and B are independently oxygen, $CH_2$ or sulfur, X is a) —$CH_2(CH_2)_m$—$N(R_2)_2$, b)

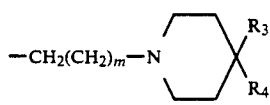

where $R_3$ is hydrogen, —$CO_2R_2$, —$CONHR_2$, —CN, —$NHR_2$, —CHO, —$(CH_2)_m$—Ar, —$NR_2Ar$ or c)

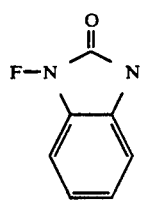

$R_4$ is hydrogen, $C_1$-$C_6$ alkyl, $C_2$-$C_8$ alkenyl, $C_2$-$C_8$ alkynyl, —$(CH_2)_m$—($C_3$-$C_8$) cycloalkyl or cycloalkenyl, —$(CH_2)_m$—Ar, —$CO_2R_2$, —$CONHR_2$, —CN or —CHO, or

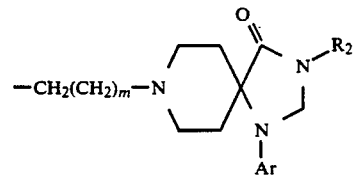

In another aspect the invention is directed toward a method for treating central nervous system and cardiovascular system disorders related to 5-HT1A neuronal activity or dopamine receptor activity comprising the administration of a therapeutically effective amount of a compound of Formula I or a pharmaceutically acceptable salt thereof to a patient in need thereof A typical dosage is from about 1-2000 mg orally or from about 0.1 to about 100 mg parenterally.

DETAILED DESCRIPTION OF THE INVENTION

The present invention is directed toward pharmaceutical compounds as represented by structural Formula I (shown on Formula Sheet) or pharmaceutically acceptable salts thereof. These compounds exhibit 5-HT1A binding and dopamine receptor binding activity and therefore are useful in the therapeutic treatment of cardiovascular system and central nervous system disorders which are related to 5-HT1A and/or dopamine pathways.

In the definition of Formula I, the parenthetical term ($C_n$-$C_m$) is inclusive such that a compound of ($C_1$-$C_8$) would include compounds of one to eight carbons and their isomeric forms. The various carbon moieties are defined as follows: $C_1$-$C_6$ alkyl refers to an aliphatic hydrocarbon chain and includes branched or unbranched forms such as methyl, ethyl, n-propyl, isopropyl, n-butyl, isobutyl, sec-butyl, t-butyl, n-pentyl, isopentyl, neopentyl, n-hexyl, and isohexyl.

$C_2$-$C_8$ alkenyl refers to an aliphatic unsaturated hydrocarbons having a double bond and includes both branched and unbranched forms such as ethenyl, 1-methyl-1-ethenyl, 1-propenyl, 2-propenyl, 1-butenyl, 2-butenyl, 3-butenyl, 2-methyl-1-butenyl, 1-pentenyl, allyl, 3-pentenyl, 4-pentenyl, 1-methyl-4-pentenyl, 3-methyl-1-pentenyl, 3-methyl-allyl, 1-hexenyl, 2-hexenyl, 3-hexenyl, 4-hexenyl, 1-methyl-4-hexenyl, 3-methyl-1-hexenyl, 3-methyl-2-hexenyl, 1-heptenyl, 2-heptenyl, 3-heptenyl, 4-heptenyl, 1-methyl-4-heptenyl, 3-methyl-1-heptenyl, 3-methyl-2-heptenyl, 1-octenyl, 2-octenyl, or 3-octenyl. $C_2$-$C_8$ alkynyl refers to an aliphatic unsaturated hydrocarbon having a triple bond and includes both branched and unbranched forms.

$C_3$-$C_8$ cycloalkyl refers to a saturated cyclic hydrocarbon such as cyclopropyl, cyclobutyl, cyclopentyl, cyclohexyl, cycloheptyl, or cyclooctyl.

$C_3$-$C_8$ cycloalkenyl refers to an unsaturated cyclic hydrocarbon having a double bond.

Halogen is meant to include fluorine, chlorine, bromine and iodine.

Ar is meant to be phenyl, pyridyl, naphthyl and indole optionally substituted with one or more of $OR_2$, halogen, —CN, —CHO, —$(CH_2)_m$—Ph, —$NO_2$, —$SR_2$ or $NHR_2$ and m is 0 to 6;

Formula I may contain a saturated or unsaturated bond at the $C_8$-$C_9$ position which is represented by a solid and dotted line.

It will be apparent to those skilled in the art that compounds of tills invention may contain chiral centers. The scope of this invention includes all enantiomeric or diastereomeric forms of Formula I compounds either in pure form or as mixtures of enantiomers or diastereomers. The therapeutic properties of the compounds may to a greater or lesser degree depend on the stereochemistry of a particular compound. Pure enantiomers as well as enantiomeric or diastereomeric mixtures are within the scope of the invention.

The compounds depicted in the Examples and Formula I Structure Sheets show A and B to be oxygen. Contemplated equivalents for oxygen are sulfur and $CH_2$.

Both organic and inorganic acids or bases can be employed to form non-toxic pharmaceutically acceptable salts of the compounds of this invention. Illustrative acids are sulfuric, nitric, phosphoric, hydrochloric, citric, acetic, lactic, tartaric, palmoic, ethanedisulfonic, sulfamic, succinic, cyclohexylsulfamic, fumaric, maleic, and benzoic acid. Illustrative bases are sodium hydroxide, lithium hydroxide, and triethylamine. These salts are readily prepared by methods known in the art.

The compounds of tills invention may be obtained by one of the following methods described below and outlined in the appropriate charts.

In clinical practice the compounds of the present invention will normally be administered in a therapeutically effective amount which is an amount sufficient to treat or cause observable modification of the cardiovascular or central nervous system disorder being treated in a patient such as mammals, including humans. The compounds of Formula I can be administered orally, rectally, or by injection, in the form of pharmaceutical preparations comprising the active ingredient either as a free base or as a pharmaceutically acceptable non-toxic acid addition salt, such as the hydrochloride, lactate, acetate, sulfamate salt, in association with a pharmaceutically acceptable carrier. The use and administration to a patient to be treated in the clinic would be readily apparent to a person of ordinary skill in the art.

In therapeutical treatment the suitable daily doses of the compounds of the invention are 1–2000 mg for oral application, preferentially 50–500 mg, and 0.1–100 mg for parenteral application, preferentially 0.5–50 mg.

Due to the influence of 5-HT1A receptor agonists on sympathetic nerve discharge, these compounds would be useful for treating hypertension, congestive heart failure, heart attack, and other disorders of the cardiovascular system.

The biological activity of these compounds indicates that they may be effective anxiolytic and anti-depressant agents. Other uses for these compounds include panic attacks, obsessive-compulsive disturbances, and senile dementia. In addition, central 5-HT receptor activation is believed to be involved in mediating sexual behavior. These compounds would be useful to stimulate sexual activity and to alleviate impotence.

The compounds of this invention are useful in the treatment of central nervous system disorders and cardiovascular system disorders as shown in physiological and biochemical tests. The methods are given as follows:

Binding: Inhibition of 3H-8-OH-DPAT binding in a bovine brain homogenate. Potency is given as nanomole (nM) dose required to inhibit 50% of DPAT binding (IC50). This test measures ability to bind to 5-hydroxytryptamine (HT1A) receptor.

For Dopamine ($D_2$): Inhibition of 3H-raclopride binding in rat striata homogenate. Potency is given as run dose required to inhibit 50% of 3H-raclopride binding ($IC_{50}$). This test measures the ability to bind to dopamine $D_2$ receptors.

Hypothermia: Starting with a dose of 30 mg/kg, four mice are injected subcutaneously with test compound. Twenty minutes later, the number of animals whose body temperature has decreased by 2° C. or more are counted. If all four animals reach criteria, the drug is considered "active", and subsequent readings are taken at 60 and 120 minutes after drug. The time for last statistically significant drug affect on mean body temperature is indicated in minutes. For all "active" compounds, doses are lowered by 0.5 log intervals until a dose which does not lower body temperature by 2° C. in any animal is found. Potency is given as mg/kg ED50 (dose required to depress temperature in two of four mice) as measured by Spearman-Karber statistics.

Biological binding and hypothermia data are shown in Table 1.

TABLE I

| | BIOLOGICAL DATA | | |
|---|---|---|---|
| Compound | $5HT_{1A}$ Binding $IC_{50}$ (nM) | Hypothermia $ED_{50}$ (mg/kg) | Dopamine D2-Receptor Binding $IC_{50}$ (nM) |
| XIa | 0.47 | 30.0 | — |
| a′ | 29.20 | — | 3.20 |
| a″ | 2.00 | 17.3 | — |
| XIb | 36.30 | 17.3 | — |
| b′ | 24.70 | 30.0 | 52.20 |
| XIc | 0.29 | — | — |
| XId | 0.17 | 0.01 | 1.53 |
| XIe | 13.50 | — | — |
| XIf | 8.40 | 17.3 | 189.70 |
| XIg | 3.70 | — | — |
| XIh | 9.60 | >30.0* | 146.70 |
| XIi | 79.30 | — | — |
| XIj* | 4.00 | 1.3 | 54.60 |
| XIk* | 26.00 | >30.0 | 349.90 |
| XIl | 2.30 | — | — |
| XIm | 1.00 | — | 0.13 |
| XIn | 267.90 | — | — |
| XIo | 279.90 | — | 97.30 |
| XIp | 11.00 | — | — | a′ position isomer of XIa
a″ is the indoline derivative where $C_7$—$C_8$ bond is saturated
b′ is the sodium salt of XIb
*hydrochloride salt form Example 1: Preparation of 2,3-dihydro-2-((4-oxo-1-phenyl-1,3,8-triazaspiro(4.5)-dec-8-yl)methyl)-7H-1,4-dioxino(2,3-e)indol-8-methyl ester, XIa The synthesis of Compound XI is represented in Chart I and is described below.

Step 1

Sodium hydride (50% oil dispersion–5.28 g, 0.11 mol) was washed with hexane (3×20 mL) and dried under a stream of nitrogen. Dry dimethylsulfoxide (65 mL) was added to the reaction flask and the resulting suspension was cooled to 0° C. under a nitrogen atmosphere. To this suspension was added a solution of 2,3-dihydroxybenzaldehyde (13.81 g, 0.10 mol) in dimethylsulfoxide (35 mL+10 mL rinse) in a slow stream via syringe. The external cooling was removed, and after stirring 1 hour at room temperature the near-black reaction mixture was treated with benzyl bromide (23.8 mL, 0.20 mol). The reaction gradually lightened in color and completely solidified in less than 1 hour. After one hour, the resulting material was physically broken-up and partitioned between ethyl acetate (2000 mL) and a 1:1 mixture of brine and water (500 mL total aqueous volume).

The organic layer was washed with additional 50% brine (2×500 mL) and dried over anhydrous magnesium sulfate. After filtration and concentration in vacuo, the residue was chromatographed on 400 g of 230–400 mesh silica gel using 15–20% ethyl acetate/hexane to give 13.6 g of compound II. Recrystallization from ethyl acetate/hexane gave an iridescent, ivory-colored solid: Rf 0.44 (40% ethyl acetate/hexane); 1H NMR (300 MHz, CDCl3) 10.15 (s, 1H, CHO), 7.5–7.1 (m, 8 H, aromatic H's), 6.05 (broad s, 1H, O—H), 5.08 (s, 2 H, O—CH2); 13C NMR (75.5 MHz, CDCl3) 189.9, 149.8, 147.9, 135.8, 129.6, 129.1, 129.0, 128.7, 125.2, 122.1, 121.5, 78.5.

Step 2

A solution of II (26.78 g, 0.117 mol) in absolute ethanol (120 mL) was treated with 1.0N aqueous sodium hydroxide (117 mL, 0.117 mol) and briefly heated to reflux under nitrogen (ca. 5 min). The black solution was cooled to room temperature and epichlorohydrin (92.6 mL, 1.16 mol) was added in a single portion. The solution was again brought to reflux using a preheated oil bath (110° C.) and maintained at that temperature for an additional 30 minutes. After cooling to room temperature, the ethanol was removed in vacuo and the aqueous residue was diluted with water (650 mL) and extracted with ethyl acetate (3×350 mL). The combined organic layers were washed once with saturated aqueous sodium chloride (150 mL) and dried over anhydrous magnesium sulfate. After filtration and concentration in vacuo, the residue was passed through a short column of silica gel using 40% ethyl acetate/hexane to remove polar, yellow material. The resulting product was dissolved in hot ether and cooled at 0° C. over the weekend to give 26.12 g (78%) of compound III as a white solid, mp 62°–63° C. The mother liquor (9.55 g of a yellow oil) was chromatographed on 600 g of 230–400 mesh silica gel using 20% ethyl acetate/hexane to give 5.93 g (18%) of additional III (total yield 96%): Rf 0.15 (20% ethyl acetate/hexane).

Step 3

A mixture of III (14.22 g, 50 mmol), cyclohexene (20.3 mL, 0.2 mol), and 10% palladium on carbon (1.40 g) in ethyl acetate (500 mL) was heated to reflux under nitrogen for 21 hour. After cooling to room temperature, the mixture was filtered through a pad of Celite, washing the filter cake well with ethyl acetate (220 mL). The filtrate was concentrated in vacuo, attempting to minimize exposure to air. The resulting residue was composed of a mixture of IV and V and was carried on directly to the final step.

Step 4

The unpurified product from the previous reaction was dissolved in ethanol (200 mL) and treated with triethylamine (14 mL, 0.10 mol) and water (200 mL). The solution was refluxed under nitrogen for 1 hour. After cooling to room temperature, the reaction mixture was directly concentrated in vacuo at 40° C. on the rotary evaporator. The resulting yellow residue was chromatographed on 500 g of 230–400 mesh silica gel with 40% ethyl acetate/hexane to give 7.77 g (80%) of V as an off-white solid. Recrystallization from ethyl acetate/hexane provided the analytical sample, mp 70°–71.5° C.: Rf 0.15 (40% ethyl acetate/hexane).

Step 5

4-Dimethylaminopyridine (0.79 g, 6.50 mmol) was added in a single portion to a solution of V (971 mg, 5.00 mmol) and tert-butyldimethylsilyl chloride (0.90 g, 6.00 mmol) in dry dichloromethane (10 mL) at 0° C. under nitrogen. The cooling bath was removed and the solution was allowed to stir overnight at room temperature. The mixture, containing a white precipitate, was diluted with dichloromethane (100 mL), washed with water (50 mL) and saturated aqueous ammonium chloride (50 mL), then dried over anhydrous sodium sulfate. After filtration and concentration in vacuo, the resulting residue was chromatographed on 50 g of 230–400 mesh silica gel using 5% ethyl acetate/hexane to give 1.30 g (84%) of VI as a colorless syrup which solidified on refrigeration, mp 32°–33° C.: $R_f$ 0.26 (5% ethyl acetate/hexane).

Step 6

A solution of sodium methoxide in methanol (25 wt %–19.1 mL, 83 mmol) was added fast dropwise over 5 minutes to a solution of VI (3.21 g, 10.4 mmol) and methyl azidoacetate (11.97 g, 104 mmol) in dry methanol (25 mL) at −22° C. (carbon tetrachloride/dry-ice) under nitrogen. The temperature was raised to −5° C. (mechanical cooling unit) and stirring was continued. After 30 minutes, additional methanol (10 mL—precooled) was added to thin the mixture, which had become quite thick and was foaming badly. After stirring overnight at −5° C., the dark reaction mixture was poured into ice-cold saturated aqueous ammonium chloride (110 mL) and extracted with ice-cold ethyl acetate (3×110 mL—it was necessary to wait out some difficult emulsions). The combined organic fractions were washed with ice-cold brine (1×55 mL) and dried over anhydrous sodium sulfate. After filtration and concentration in vacuo, the resulting residue (minus 8% removed for exploratory work) was adsorbed onto 15 g of 230–400 mesh silica gel (from a dichloromethane solution), then chromatographed on 300 g of 230–400 mesh silica gel using 2.5% ethyl acetate/hexane to give 2.81 g (72%) of VII as a yellow oil. The material solidified below room temperture; at room temperature the material was a semi-solid: $R_f$ 0.25 (5% ethyl acetate/hexane). A solution of VII (16.5 g, 40.7 mmol) in o-xylene was refluxed (oil bath preheated to 180° C.) under nitrogen for 1.5 hours. The solvent was removed in vacuo at 60° C. to give a yellow solid residue which was recrystallized from hexane (aprox. 200 mL) to give 11.6 g (75%) of VIII as fine, white needles, mp 141.5°–142.5° C.: $R_f$ 0.16 (10% ethyl acetate/hexane).

Step 7

A solution of VIII (3.78 g, 10.0 mmol) in dry tetrahydrofuran (35 mL) was treated with 1M tetra-n-butylammonium fluoride in tetrahydrofuran (11.0 mL, 11.0 mmol) at room temperture under nitrogen. After stirring for 1 hour and 20 minutes, the cloudy mixture was poured into saturated aqueous ammonium chloride (115 mL) using methanol to aid in the transfer process. The organic solvents were removed in vacuo and the aqeous remainder was further diluted with water then extracted with ethyl acetate (3×70 mL). The combined organic layers were washed with brine (25 mL), then dried over anhydrous magnesium sulfate. After filtration and concentration, the resulting residue was chromatographed on 70 g of 230–400 mesh silica gel using 40% ethyl acetate/hexane until IX began to elute, and then using 75% ethyl acetate/hexane to pick up the tailing. Thus was obtained 2.60 g (99%) of IX as a white solid, mp 158°–160° C. (from ethyl acetate/hexane): $R_f$ 0.17 (40% ethyl acetate/hexane).

Step 8 p-Toluenesulfonyl chloride (660 mg, 3.46 mmol) was added in a single portion to a solution of IX (759 mg, 2.88 mmol) and 4-dimethylaminopyridine (457 mg, 3.74 mmol) in dry dichloromethane at 0° C. under nitrogen. The cooling bath was removed and the solution was stirred overnight at room temperature. The white solid present after this time was collected and washed with a minimum amount of dichloromethane to give 960 mg (80%) of the compound X, mp 204°-206° C. (ethyl acetate/hexane).

Step 9

A mixture of X (3.17 g, 7.60 mmol), 1-phenyl-1,3,8-triazaspiro[4.5]decan-4-one (5.27 g, 22.8 mmol), and powdered potassium carbonate (5.25 g, 38.0 mmol) in dry pyridine (75 mL) was heated at 75° C. for 24 h under nitrogen. After cooling to room temperature, the black mixture was diluted with dichloromethane (1 vol.) and filtered through Celite. The black tar residing on top of the filter cake was washed/triturated with dichloromethane as well as possible. The residue obtained on concentration of the filtrate in vacuo was taken up in a large volume of dichloromethane and chromatographed on 300 g of 230-400 mesh silica gel using 75% ethyl acetate/hexane (a fair amount of undissolved XIa may have simply been deposited at the head of the column) to give 2.01 g (56%) of XIa as a pale yellow, beige solid. (The yellow coloration was easily removed on trituration with most organic solvents) Recrystallization from methanol (a large volume of methanol is required, then reduction of the volume by one-half until precipitation is evident on the hot plate) gave an off-white solid with vague melting point: $R_f$ 0.18 (75% ethyl acetate/hexane); IR (mull) 3320, 2954, 2924, 2856, 1714, 1690, 1529, 1259, 1237, 1217 cm$^{-1}$; $^1$H NMR (300 MHz, DMSO-d6) 11.85 (broad s, 1H, indole N—H), 8.66 (broad s, 1H, lactam N—H), 7.25 (t, J=7.6 Hz, 2 H, phenyl meta H's), 7.00 (d, J=2.0 Hz, 1H, vinylic H), 6.95 (m, 4 H, phenyl ortho H's and aromatic H's), 4.58 (s, 2 H, N—CH2—N), 4.49 (m, 1H, O—CH), 4.36 (m, 1H, O—CH2a), 4.05 (dd, J=11.5 Hz, J=6.7 Hz, 1H, O—CH2b), 3.85 (s, 3 H, O—CH3), 3.0-2.5 (m, 8 H, N—CH2's and N—C—CH2a's), 1.60 (m, 2 H, N—C—CH2b's); $^{13}$C NMR (300 MHz, DMSO-d6) 177.2, 162.4, 144.3, 135.9 (overlap), 134.8, 129.9, 127.5, 119.1, 118.5, 117.6, 115.1, 106.0, 104.6, 72.5, 67.2, 59.6, 58.8, 58.5, 52.6, 51.4 and 50.5 (differentiation of the piperidine-ring carbons alpha to the nitrogen), 29.4; HRMS, m/e 476.2076 ($C_{26}H_{28}N_4O_5$ requires 476.2060); Anal. Calcd for $C_{26}H_{28}N_4O_5$ 0.5 CH$_3$OH: C, 64.62; H, 6.14; N, 11.38.

Found: C, 64.85; H, 5.98; N, 11.27.

The preparation of Examples 2-6 are structurally represented on Chart 11 for Compounds XIb through XIf.

Example 2: Preparation of 7H,4-Dioxino(2,3-e)indole-8-carboxylic acid, 2,3-dihydro-2-((4-oxo-1-phenyl-1,3,8-triazaspiro(4.5)dec-8-yl), XIb A suspension of XIa as prepared in Example 1 (200 mg, 0.40 mmol) in methanol (2 mL) was treated with a solution of lithium hydroxide monohydrate (34 mg, 0.80 mmol) in water (1 mL). The heterogeneous mixture was heated under nitrogen at 60° C. for 4.5 hours during which time a clear amber solution was gradually obtained. After cooling to room temperature, the solution was diluted with water (6 mL) and acidified to pH 7 with aqueous 1N hydrochloric acid. The voluminous white solid which precipitated was filtered only with great difficulty—it was subsequently determined that a more manageable solid results if the methanol is first removed in vacuo. The total amount of material was redissolved using aqueous acetone. After concentration in vacuo, the residue was triturated with water to extract-out the inorganic salts and the resulting off-white solid was filtered and washed with water. Recrystallization of this material was not possible and so the product was purified by reprecipitation: a suspension in water was treated with aqueous 1N sodium hydroxide until a clear solution was obtained (pH 12), then the pH was adjusted to 7 with aqueous 1N hydrochloric acid. The resulting solid was filtered, washed with water, and air-dried on the filter funnel for a considerable time before it could be manipulated to give 145 mg (actual yield greater than 90%) of XIb as a beige powder (decomposes at approx. 230° C. with gas evolution): $R_f$ 0.20 (100:50:5 chloroform/methanol/concentrated aqueous ammonium hydroxide); $^1$H NMR (300 MHz, DMSO-d6) 11.59 (broad s, 1H, indole N—H), 8.70 (broad s, 1H, CON—H), 7.22 (t, J 7.7 Hz, 2 H, Ph meta H's), 6.89 (m, 5 H, Ph ortho H's and vinylic H and aromatic H's), 6.73 (t, J 7.2 Hz, 1H, Ph para H), 4.59 (s, 2 H, N—CH2—N), 4.55 (m, 1H, O—CH), 4.36 (broad d, J=10.3 Hz, 1H, O—CH2a), 4.05 (dd, J=11.2 Hz, J=6.72 Hz, 1H, O—CH2b), 3.1-2.55 (m, 8 H, N—CH2's and N—C—CH2a's), 1.63 (m, 2 H, N—C—CH2b's); $^{13}$C NMR (75.5 MHz, DMSO-d6) 176.2, 163.0, 143.3, 134.8, 133.5, 129.0, 118.3, 117.6, 115.8, 114.2, 105.0, 102.9, 71.3, 66.2, 58.7, 57.9, 57.5, 50.3, 49.5, 28.2; HRMS (FAB), M/C 463.1987 [$C_{25}H_{27}N_4O_5$ (M+1) requires 463.1981]; Anal. Calcd for $C_{25}H_{26}N_4O_5$ 1.25 H$_2$O: C, 61.91; H, 5.92; N, 11.55. Found: C, 61.90; H, 5.88; N, 11.54.

Example 3: Preparation of 7H-1,4-Dioxino(2,3-e)indole-8-carboxamide, 2,3-dihydro-2-((4-oxo-1-phenyl-1,3,8-triazaspiro(4.5)dec-8-yl)methyl)-, XIc A suspension of XIa (1.00g, 1.92 mmol) and sodium cyanide (10 mg, 0.20 mmol) in 16% methanolic ammonia (100 mL) was heated in a pressure tube (Ace #15 thread) for 5 days at 100° C. The dark homogeneous mixture was cooled and concentrated in vacuo. The residue was taken-up in dichloromethane plus the minimum amount of methanol and chromatographed on 50 g of 230-400 mesh silica gel using 75% ethyl acetate/hexane until a small amount of unreacted XIa was recovered, followed by 2% methanol/ethyl acetate to give a pale-yellow solid. Recrystallization from methanol gave 473 mg (53%) of XIc as a white solid; crystallization of the mother liquor from ethyl acetate gave an additional 85 mg of XIc as a beige solid: $R_f$ 0.16 (1% methanol/ethyl acetate); IR (mull) 2953, 2925, 2867, 2855, 1706, 1676, 1599, 1515, 1501, 1373 cm$^{-1}$; $^1$H NMR (300 MHz, DMSO-d6) 11.41 (broad s, 1H, indole N—H), 8.66 (broad s, 1H, CON—H), 7.91 (broad s, 1H, NH2a), 7.26 (broad s, 1H, NH2b), 7.25 (t, J=7.4 Hz, 2 H, meta phenyl H's), 7. 1 0 (d, J=1.7 Hz, 1H, vinyl H), 6.87 (m, 3 H, ortho phenyl H's and aromatic H), 6.76 (m, 2 H, para phenyl H and aromatic H), 4.58 (s, 2 H, N—CH2—N), 4.45 (m, 1H, O—CH), 4.38 (m, 1H, O—CH2a), 4.04 (m, 1H, O—CH2b), 3.05-2.5 (m, 8 H, N—CH2's and N—C—CH2a's), 1.58 (m, 2 H, N—C—CH2b's); $^{13}$C NMR (75.5 MHz, DMSO-d6) 176.2, 162.6, 143.3, 134.9, 134.7, 132.9, 131.3, 129.0, 118.3, 117.6, 114.8, 114.3, 104.8, 99.6, 71.7, 66.3, 58.6, 57.9, 50.6, 49.6, 28.4; HRMS, m/e 461.2074 ($C_{25}H_{27}N_5O_4$ requires 461.2063); Anal. Calcd for $C_{25}H_{27}N_5O_4$ 0.5 EtOAc: C, 64.15; H, 6.18; N, 13.85. Found: C, 63.84; H, 6.46; N, 13.98.

Example 4: Preparation of 7H-1,4-Dioxino(2,3-e)indole-8-carbonitrile, 2,3-dihydro-2-((4-oxo-1-phenyl-1,3,8-triazaspiro(4.5)dec-8-yl)methyl)-, XId A solution of XIc (61 mg, 0.121 mmol) in dry tetrahydrofuran (4 mL) under nitrogen at room temperature was treated with the inner salt of methyl (carboxysulfamoyl)triethylammonium hydroxide (Burgess reagent) (32 mg, 0.133 mmol). After stirring 1 hour, a second portion of Burgess reagent (32 mg, 0.133 mmol) was added and staring was continued for an additional hour. The mixture was concentrated in vacuo and the residue was chromatographed on 5 g of 230–400 mesh silica gel using 3.5% methanol/dichloromethane to give 51 mg (94%) of XId as a white solid. The material could not be successfully recrystallized, and yielded the most workable solid upon concentration in vacuo from its toluene solution: $R_f$ 0.35 (5% methanol/dichloromethane); IR (mull) 2953, 2922, 2867, 2855, 1707, 1519, 1503, 1457, 1373, 1242, and 2221 cm$^{-1}$; $^1$H NMR (300 MHz, CDCl$_3$) 9.33 (broad s, 1H, N—H), 7.24 (m, 3 H, meta phenyl H's and CON—H), 7.05 (d, J=1.4 Hz, 1H, vinylic H), 6.97 (d, J=8.8 Hz, 1H, aromatic H), 6.86 (m, 4 H, ortho phenyl H's and aromatic H and para phenyl H), 4.74 (s, 2 H, N—CH$_2$—N), 4.52 (m, 1H, O—CH), 4.40 (dd, J=11.4 Hz, J=2.2 Hz, 1H, O—CH$_2$a), 4.09 (dd, J=11.4 Hz, J=6.8 Hz, 1H, O—CH$_2$b), 3.2–2.6 (m, 8 H, N—CH$_2$a's and N—C—CH$_2$a's), 1.78 (m, 2 H, N—C—CH$_2$b's); $^{13}$C NMR (75.5 MHz, CDCl$_3$) 177.9, 142.9, 136.2 (possible overlap), 135.3, 133.2 (possible overlap), 129.2, 119.1, 117.9, 115.5, 114.3. 110.6, 105.5, 104.0, 71.9, 66.9, 59.2, 59.0, 58.3, 50.8, 49.9, 29.1, 29.0; HRMS, m/e 443.1964 (C$_{25}$H$_{25}$N$_5$O$_3$ requires 443.1957).

Example 5: Preparation of 7H-1,4-Dioxino(2,3-e)indole-8-carboxylic acid, 2,3-dihydro-2-((4-oxo-1-phenyl-1,3,8-triazaspiro(4.5)dec-8-yl)methyl)-, butyl ester, XIe A suspension of XIa (95 mg, 0.200 mmol) and 1,8-diazabicyclo[5.4.0]undec-7-ene (3 mg, 0.020 mmol) in dry 1-butanol (volume varied from 2–8 mL on draining of the Soxhlet) was refluxed under nitrogen using a Soxhlet extractor containing 3 A molecular sieves (1.8 g) in a cellulose thimble. After 31 h, refluxing was stopped and the solution was allowed to stand overnight at room temperature. The 1-butanol was removed in vacuo and the solid residue was dissolved in dichloromethane (approx. 15 mL) and chromatographed on 10 g of 230–400 mesh silica gel using 75% ethyl acetate/hexane to give a white solid (105 mg). The solid was recrystallized from ethyl acetate to give 79 mg (76%) of XIe as very fine, white needles, mp 203.5°–204.5° C.: $R_f$ 0.21 (75% ethyl acetate/hexane); IR (mull) 3322, 2953, 2926, 2863, 2854, 1717, 1695, 1253, 1207, 770 cm$^{-1}$; $^1$H NMR (300 MHz, DMSO-d6) 11.79 (broad s, 1H, indole N—H), 8.66 (broad s, 1H, amide N—H), 7.24 (t, J=7.3 Hz, 2 H, phenyl meta H's), 6.99 (s, 1H, vinylic H), 6.95–6.75 (m, 4 H, aromatic H's and phenyl ortho H's), 6.75 (t, J=7.3 Hz, 1H, phenyl para H), 4.59 (s, 2 H, N—CH$_2$—N), 4.5–4.35 (m, 2 H, O—CH and O—CH$_2$a), 4.28 (t, J=6.3 Hz, 2 H, butyl O—CH$_2$), 4.04 (dd, J=11.0 Hz, J 6.7 Hz, 1 H, O—CH$_2$b), 3.0–2.5 (m, 8H, N—CH$_2$'s and N—C—CH$_2$a's), 1.75–1.35 (m, 6 H, N—C—CH$_2$b's and CH$_2$'s), 0.94 (t, J=7.2 Hz, 3H, CH$_3$); $^{13}$C NMR (75.5 MHz, DMSO-d6) 178.0, 162.9, 145.1, 136.8, 135.6, 130.7, 128.6, 119.9, 119.3, 118.3, 115.9, 106.8, 105.3, 73.3, 68.1, 65.7, 60.4, 59.7, 59.4, 52.2, 51.4, 32.1, 30.2, 20.4, 15.3; HRMS, m/e 518.2542 (C$_{29}$H$_{34}$N$_4$O$_5$ requires 518.2529);

Anal. Calcd for C$_{29}$H$_{34}$N$_4$O$_5$: C, 67.16; H, 6.61; N, 10.80. Found: C, 67.08; H, 6.76; N, 10.83.

Example 6: Preparation of 7H-1,4-Dioxino(2,3-e)indole-8-carboxylic acid, 2,3-dihydro-2-((4-oxo-1-phenyl-1,3,8-triazaspiro(4.5)dec-8-yl)methyl)-, phenylmethyl ester, XIf A suspension of XIa (95 mg, 0.200 mmol) and 1,8-diazabicyclo[5.4.0]undec-7-ene (3 mg, 0.020 mmol) in dry benzyl alcohol (2 mL) and toluene (volume varied from 1–7 mL on draining of the Soxhlet) was refluxed under nitrogen overnight using a Soxhlet extractor containing 3 A molecular sieves (1.8 g) in a cellulose thimble. The toluene and the benzyl alcohol were removed in vacuo (the alcohol required Kugelrohr distillation at 90° C./0.1 mmhg), and the residue, applied in dichloromethane, was chromatographed on 10 g of 230–400 mesh silica gel using 75% ethyl acetate/hexane to give a white solid (105 mg). The solid was recrystallized from acetone to give 68 mg (61%) of XIf as very fine, white needles, mp 217°–219° C.: $R_f$ 0.19 (75% ethyl acetate/hexane); IR (mull) 3350, 2954, 2924, 2855, 1717, 1710, 1701, 1253, 1212, 1198 cm$^{-1}$; $^1$H NMR (300 MHz, DMSO-d6) 11.86 (broad s, 1H, indole N—H), 8.66 (broad s, 1H, amide N—H), 7.5–7.3 (m, 5 H, benzyl Ph H's), 7.23 (t, J=7.1 Hz, 2 H, meta phenyl H's), 7.05 (s, 1H, vinylic H), 6.95–6.8 (m, 4 H, ortho phenyl H's and aromatic H's), 6.73 (t, J=7.2 Hz, 1H, para phenyl H), 5.37 (s, 2 H, Ph—CH.), 4.58 (s, 2 H, N—CH$_2$—N), 4.47 (m, 1H, O—CH), 4.37 (m, 1H, O—CH$_2$a), 4.05 (m, 1H, O—CH$_2$b), 3.0–2.45 (m, 8 H, N—CH$_2$'s and N—C—CH$_2$a's), 1.57 (m, 2 H, N—C—CH$_2$b's); $^{13}$C NMR (75.5 MHz, DMSO-d6) 178.0, 162.6, 145.1, 137.9, 136.8, 135.7, 130.7, 130.2, 129.8, 129.7, 128.3, 120.0, 119.3, 118.5, 115.9, 106.8, 105.8, 73.7, 68.1, 67.4, 60.4, 59.7, 59.4, 52.2, 51.4, 30.2; HRMS, m/e 552.2377 (C$_{32}$H$_{32}$N$_4$O$_5$ requires 552.2373);

Anal. Calcd for C$_{32}$H$_{32}$N$_4$O$_5$: C, 69.55; H, 5.84; N, 10.14. Found: C, 69.25; H, 5.92; N, 10.11.

Examples 7–11 are structurally represented in Chart III for compounds XIg-k.

Example 7: Preparation of 7H-1,4-Dioxino(2,3-e)indole-8-carboxylic acid, 2-((4-(2,3-dihydro-2-oxo-1H-benzimidazol-1-yl)-1-piperidinyl)methyl)-2,3-dihydro-, methyl ester, monohydrochloride, XIg A solution of X (125 mg, 0.300 mmol), 4-(2-keto-1-benzimidazolinyl)-piperidine (196 mg, 0.900 mmol), and powdered, anhydrous potassium carbonate (207 mg, 1.50 mmol) in dry pyridine (3 mL) was stirred under nitrogen at 75° C. for 24 h. After cooling to room temperature, the black mixture was diluted with dichloromethane and filtered through non-absorbent cotton. The filtrate was concentrated in vacuo, allowing a small amount of pyridine to remain. The residue was taken-up in a large volume of dichloromethane and chromatographed on 9 g of 230–400 mesh silica gel using 100% ethyl acetate to give 63 mg (45%) of XIg as a light-yellow solid: $R_f$ 0.15 (100% ethyl acetate); $^1$H NMR (300 MHz, DMSO-d6) 11.87 (broad s, 1H, amide N—H), 10.88 (broad s, 1H, indole N—H), 7.3–6.8 (m, 7 H, aromatic H's and vinylic H), 4.50 (m, 1H, O—CH), 4.37 (d, J=10.7 Hz, O—CH$_2$a), 4.18 (m, 1H, N—CH), 4.05 (dd, J=11.4 Hz, J=6.8 Hz, 1H, O—CH$_2$b), 3.86 (s, 3 H, O—CH$_3$), 3.18 (broad d, J=10.0 Hz, 1H, O—C—CH$_2$a—N), 3.04 (broad d, J=8.1 Hz, 1H, O—C—CH$_2$b—N), 2.72 (broad d, J=5.6 Hz, 2 H, N—CH$_2$a's), 2.55–2.2 (m, 4H, N—CH$_2$b's and N—C—CH$_2$a's), 1.64 (m, 2H, N—C—CH$_2$b's); 13N NMR (75.5 MHz, DMSO-d6) 163.2, 155.5, 136.8, 135.6, 130.9, 130.1, 128.4, 122.2, 122.1, 119.9, 118.4, 110.5, 110.4, 106.8, 105.5, 73.5, 68.0, 59.2, 55.7, 54.6, 53.4, 51.7, 30.5, 30.4. The hydrochloride salt was prepared by treating a suspension of XIg in methanol with 40% methanolic hydrogen chloride. The salt precipitated as a pale yellow solid, mp approx. 300° C. (dec): HRMS, m/c 462.1915 ($C_{25}H_{26}N_4O_5$ requires 462.1903); Anal. Calcd for $C_{25}H_{26}N_4O_5$ HCl 0.5 MeOH: C, 59.47; H, 5.68; N, 10.88. Found: C, 59.49; H, 5.75; N, 10.98.

Example 8: Preparation of 7H-1,4-Dioxino(2,3-e)indole-8-carboxylic acid, 2-((4-(ethoxycarbonyl-1-piperidinyl)methyl)-2,3-dihydro-, methyl ester, monohydrochloride, XIh A solution of X (291 mg, 0.700 mmol), ethyl isonipecotate (329 mg, 2.10 mmol), and powdered, anhydrous potassium carbonate (482 mg, 3.50 mmol) in dry pyridine (7 mL) was stirred overnight under nitrogen at 75° C. After cooling to room temperature, the black mixture was concentrated in vacuo and the residue was taken-up in water (50 mL) and extracted with ethyl acetate (3×20 mL). The combined organic layers were washed with bane (10 mL), then dried over anhydrous sodium sulfate. After filtration and concentration, the residue (applied in dichloromethane) was chromatographed on 20 g of 230-400 mesh silica gel using 40% ethyl acetate/hexane to give, Secondly was isolated 150 mg (53%) of XIh also as a beige solid, mp 153°-154.5° C. (benzene). Treatment of this material with methanolic hydrogen chloride provided the hydrochloride salt as a white solid after recrystallization from methanol/ethyl acetate. For the free-base: $R_f$ 0.17 (40% ethyl acetate/hexane); IR (mull) 3341, 2954, 2925, 2855, 1735, 1687, 1528, 1446, 1257, 1217 $cm^{-1}$; $^1H$ NMR (300 MHz, CDCl3) 9.34 (broad s, 1H, N—H), 7.21 (m, 1H, vinylic H), 6.90 (m, 2 H, aromatic H's), 4.43 (m, 1H, O—CH), 4.32 (d, J=11.3 Hz, 1H, O—CH$_2$a), 4.14 (quart, J=7.2 Hz, 2 H, ethyl O—CH$_2$), 4.03 (dd, J=11.3 Hz, J=6.9 Hz, 1H, O—CH$_2$b), 3.93 (s, 3 H, O—CH$_3$), 3.05 (m, 1H, O—C—CH$_2$a—N), 2.91 (m, 1H, O—C—CH$_2$b—N), 2.70 (ddd, J=20.2 Hz, J=13.5 Hz, J=5.7 Hz, 2 H, N—CH$_2$a), 2.35-2.15 (m, 3H, N—CH$_2$b and CH), 2.0-1.7 (m, 4 H, CH$_2$a's and CH$_2$b's), 1.25 (t, J=7.2 Hz, 3 H, CH$_3$); $^{13}H$ NMR (75.5 MHz, CDCl3) 175.0, 162.3, 135.7, 135.5, 133.4, 126.6, 118.9, 117.1, 105.2, 104.3, 71.9, 66.8, 60.2, 58.5, 54.1, 53.1, 51.8, 40.8, 28.3, 28.2, 14.1; HRMS, m/e 402.1802 ($C_{21}H_{26}N_2O_6$ requires 402.1791); Anal. Calcd for $C_{21}H_{26}N_2O_6$: C, 62.68; H, 6.51; N, 6.96. Found: C, 62.61; H, 6.70; N, 6.88. For the hydrochloride salt: Anal. Calcd for $C_{21}H_{26}N_2O_6$ HCl: C, 57.47; H, 6.20; N, 6.38. Found: C, 57.14; H, 6.27; N, 6.47.

Example 9: Preparation of 7H-1,4-Dioxino(2,3-e)indole-8-carboxylic acid, 2-((4(aminocarbonyl)-4-(phenylamino)-1-piperidinyl)methyl)-2,3-dihydro-, methyl ester, XIi A solution of X (125 mg, 0.300 mmol), 4-anilino-4-carbamylpiperidine (132 mg, 0.600 mmol), and powdered, anhydrous potassium carbonate (207 mg, 1.50 mmol) in dry pyridine (3 mL) was stirred overnight under nitrogen at 75° C. After cooling to room temperature, the black mixture was diluted with dichloromethane and filtered through non-absorbent cotton. The filtrate was concentrated in vacuo, allowing a small amount of pyridine to remain. The residue was chromatographed on 8 g of 230-400 mesh silica gel using 5% methanol/ethyl acetate to give 80 mg (58%) of XIi as a yellow-brown solid due to bleeding of an unknown dark substance on the column. The material was recrystalized from methanol/ethyl acetate to give a flocculent, off-white solid, mp 240°-241° C. (dec): $R_f$ 0.14 (5% methanol/ethyl acetate); IR (mull) 3314, 2954, 2927, 2855, 1685, 1655, 1529, 1449, 1264, 1246 $cm^{-1}$; 1H NMR (300 MHz, DMSO-d6) 11.85 (broad s, 1H, indole N—H), 7.22 (broad s, 1H, NH$_2$a), 7.10 (broad s, 1H, NH$_2$b), 7.06 (m, 2 H, meta Ph H's), 6.98 (s, 1H, vinylic H), 6.92 (d, J=8.8 Hz, 1 H, aromatic H), 6.87 (d, J=8.7 Hz, 1H, aromatic H), 6.59 (m, 3 H, ortho and para Ph H's), 4.43 (m, 1H, O—CH), 4.29 (broad d, J=10.8 Hz, 1H, O—CH$_2$a), 3.99 (m, 15, 0-CH$_2$b), 3.85 (s, 3 H, O—CH$_3$), 2.85-2.3 (m, 6 H, N—CH$_2$'s), 2.1-1.8 (m, 4 H, CH$_2$a's and CH$_2$b's); 13C NMR (75.5 MHz, DMSO-d6) 179.5, 163.3, 147.3, 136.8, 135.7, 130.3, 128.4, 120.0, 118.5, 118.3, 116.5, 106.9, 105.5, 73.5, 68.1, 59.6, 58.6, 53.5, 51.3, 50.6, 33.4, 33.0; HRMS, m/e 464.2058 ($C_{25}H_{28}N_4O_5$ requires 464.2060);, Anal. Calcd for $C_{25}H_{28}N_4O_5$: C, 64.64; H, 6.08; N, 12.06. Found: C, 64.47; H, 6.26; N, 12.13.

Example 10: Preparation of 7H-1,4-Dioxino(2,3-e)indole-8-carboxylic acid, 2,3-dihydro-2-((3-phenylpropyl)amino)methyl)-, methyl ester, monohydrochloride, XIj A solution of X (162 mg, 0.388 mmol) and potassium carbonate (107 mg, 0.776 mmol) in 3-phenyl-1-propylamine (1.0 mL) was stirred under nitrogen at 75° C. for 5 h. A thick gel developed during tins time. After cooling to room temperature, the mixture was taken-up in water (25 mL) and extracted with dichloromethane (3×10 mL). The combined organic layers were washed with water (5 mL) and dried over anhydrous sodium sulfate. After concentration in vacuo to remove the dichloromethane, the excess of amine was distilled-off (Kugelrohr) at 80° C. and 0.1 mmhg. The residue was chromatographed on 20 g of 230-400 mesh silica gel using 40-75% ethyl acetate/hexane to give 70 mg (47%) of XIj as a colorless syrup which solidified to a white solid: $R_f$ 0.23 (15% acetone/hexane); $^1H$ NMR (300 MHz, CDCl3) 9.31 (broad s, 1H, indole N—H), 7.22 (m, 6 H, phenyl H's and vinylic H), 6.92 (d, J=8.8 Hz, 1H, aromatic H), 6.88 (d, J=8.8 Hz, 1H, aromatic H), 4.42 (m, 1H, O—CH), 4.30 (dd, J=11.4 Hz, J=2.2 Hz, 1H, O—CH$_2$a), 4.06 (dd, J=11.4 Hz, J=7.0 Hz, 1H, O—CH$_2$b), 3.92 (s, 3 H, O— CH$_3$), 2.99 (dd, J=12.6 Hz, J=7.0 Hz, 1H, N—CH$_2$a—C—O), 2.90 (dd, J=12.6 Hz, J=4.6 Hz, 1H, N—CH$_2$b—C—O), 2.69 (m, 4 H, N—CH$_2$ a Ph—CH$_2$), 1.85 (quint, J=7.6 Hz, 2 H, CH$_2$), 1.63 (broad s, 1H, N—H); 13C NMR (75.5 MHz, CDCl3) 162.3, 141.9, 135.7, 135.6, 133.4, 128.3, 128.2, 126.7, 125.7, 118.9, 117.2, 105.2, 104.4, 73.0, 66.4, 51.8, 49.8, 49.3, 33.4, 31.5.

Example 11: Preparation of 7H-1,4-Dioxino(2,3-e)indole-8-carboxamide, 2,3-dihydro-N-(3-phenylpropyl)-2-(((3-phenylpropyl)amino)methyl)-, monohydrochloride, XIk A solution of X (162 mg, 0.388 mmol) and potassium carbonate (107 mg, 0.776 mmol) in 3-phenyl-1-propylamine (1.0 mL) was stirred under nitrogen at 75° C. for 5 h. A thick gel developed during this time. After cooling to room temperature, the mixture was taken-up in water (25 mL) and extracted with dichloromethane (3×10 mL). The combined organic layers were washed with water (5 mL) and dried over anhydrous sodium sulfate. After concentration in vacuo to remove the dichloromethane, the excess of amine was distilled-off (Kugelrohr) at 80° C. and 0.1 mmhg. The residue was chromatographed on 20 g of 230-400 mesh silica gel using 40-75 % ethyl acetate/hexane to give 82 mg (44%) of XIk as a white, waxy solid: 0.14 (15% acetone/hexane); $^1H$ NMR (300 MHz, CDCl3) 10.10 (broad s, 1H, indole N—H), 7.4-7.1 (m, 10 H, Ph H's), 6.89 (d, J=8.8 Hz, 1H, aromatic H), 6.85 (d, J=8.8 Hz, 1H, aromatic H), 6.75 (d, J=1.7 Hz, 1 H, vinylic H), 6.24 (broad t, J=5.8 Hz, 1H, O=CN—H), 4.39 (m, 1H, O—CH), 4.29 (dd, J=11.4 Hz, J=2.1 Hz, 1H, O—CH$_2$a), 4.05 (dd, J=11.4 Hz, J=7.0 Hz, 1H, O—CH$_2$b), 3.51 (quart, J=6.7 Hz, 2 H, O=CN—CH$_2$), 2.98 (dd, J=12.6 Hz, J=7.1 Hz, 1H, O—C—CH$_2$a—N), 2.88 (dd, J=12.6 Hz, J=4.7 Hz, 1H, O—C—CH$_2$b—N), 2.71 (m, 6 H, N—CH$_2$ and Ph—CH$_2$'s), 1.95 (quint, J=7.3 Hz, 2 H, O=C-N—C—CH$_2$), 1.84 (quint, J=7.6 Hz, 2 H, CH$_2$); $^{13}$C NMR (75.5 MHz, CDCl$_3$) 161.6, 141.9, 141.2, 135.5, 135.2, 133.0, 130.4, 128.5, 128.3, 126.0, 125.7, 118.8, 115.9, 104.7, 98.2, 73.0, 66.5, 49.9, 49.4, 39.3, 33.4, 33.3, 31.6, 31.1.

Example 12: Preparation of 1,3,8-Triazaspiro(4.5)decan-4-one, 8-((2,3-dihydro-7H-1,4-dioxino(2,3-e)indol-2-yl)methyl)-1-phenyl, XIm Preparation of XIm is structurally represented in Chart IV.

Step 1

A solution of lithium hydroxide monohydrate (190 mg, 4.52 mmol) in water (7 mL) was added to a solution of IX (595 mg, 2.26 mmol) in methanol (14 mL) under nitrogen and the solution was heated at 60° C. for 1 hour. The methanol was removed in vacuo and additional water (20 mL) was added to the aqueous remainder. The pH was adjusted to 2 with 1N hydrochloric acid and the resulting thick, white precipitate was filtered and washed well with water. After air-drying for some time, further drying in vacuo gave 540 mg (96%) of XII as a white powder. Recrystallization from ethyl acetate/ethanol/hexane (ethanol was added to a suspension of XII in ethyl acetate until a clear solution was obtained, followed by the addition of 1 vol. of hexane and subsequent cooling) gave an amorphous white solid.

Step 2

A round-bottom flask containing solid XII (407 mg, 1.63 mmol) under nitrogen was lowered into an oil bath preheated at 240° C. The temperature was raised to 257° C. and maintained there for 30 min, during which time gas evolution occurred. After cooling to room temperature, the resulting resin was dissolved in ethyl acetate, and the solution concentrated in vacuo. The residue was taken up in 75% ethyl acetate/hexane and chromatographed on 40 g of 230–400 mesh silica gel using 40% ethyl acetate/hexane to give 208 mg (62%) of XIII as a near colorless syrup: R$_f$0.23 (40% ethyl acetate/hexane).

Step 3 p-Toluenesulfonyl chloride (212 mg, 1.11 mmol) was added in a single portion to a solution of XIII (190 mg, 0.926 mmol) and 4-dimethylaminopyridine (147 mg, 1.20 mmol) in dry dichloromethane (9 mL) at 0° C. under nitrogen. The cooling bath was removed and the solution was stirred at room temperature for 23 hours. The mixture was transferred to a separatory funnel with additional dichloromethane (15 mL) and washed with water (1×5 mL), saturated aqueous copper sulfate (2×5 mL), and water (1×5 mL), then dried over anhydrous sodium sulfate. After filtration and concentration in vacuo, the resulting greenish solid was adsorbed onto 1 g of 230–400 mesh silica gel (from ethyl acetate) and chromatographed on 20 g of 230–400 mesh silica gel using 25–30% ethyl acetate/hexane. The syrup initially obtained was dissolved in 60% ethyl acetate/hexane (several mL's) where 200 mg of XIV was deposited as a white, crystalline solid, mp 145–145.5° C.; the essentially pure mother liquor amounted to 90 mg (total yield 87%): R$_f$0.32 (40% ethyl acetate/hexane).

Step 4

A solution of XIV (237 mg, 0.659 mmol), 1-phenyl-1,3,8-triazaspiro[4.5]decan-4-one (458 mg, 1.98 mmol), and powdered, anhydrous potassium carbonate (456 mg, 3.30 mmol) in dry pyridine (7 mL) was heated at 75° C. under nitrogen overnight. The black mixture was diluted with dichloromethane (1 vol) and filtered through Celite, washing the black sludge well with dichloromethane. The filtrate was concentrated in vacuo (a slight amount of pyridine was allowed to remain), and the residue was taken-up in a large volume of dichloromethane and chromatographed on 20 g of 230–400 silica gel using 75% ethyl acetate/hexane to give 152 mg (55%) of XIm as a yellowed solid; for analysis, recrystallization from ethyl acetate/ethanol/hexane gave a pale yellow-tan solid, mp 228–230 (dec): R$_f$0.17 (75% ethyl acetate/hexane); 2955, 2925, 2854, 1711, 1511, 1497, 1456, 1360, 1236, 1094 cm$^{-1}$; $^1$H NMR (300 MHz, DMSO-d6) 10.93 (broad s, 1H, indole N—H), 8.65 (broad s, 1H, lactam N—H), 7.25 (t, J=7.7 Hz, 2 H, phenyl meta H's), 7.19 (t, J=2.7 Hz, 1H, vinylic H), 6.86 (m, 3 H, phenyl ortho H's and aromatic H), 6.76 (t, J=7.3 Hz, 1H, phenyl para H), 6.65 (d, J=8.6 Hz, 1H, aromatic H), 6.31 (m, 1H, vinylic H), 4.58 (s, 2 H, N—CH$_2$—N), 4.43 (m, 1 H, O—CH), 4.34 (m, 1 H, O—CH$_2$a), 4.02 (dd, J=11.3 Hz, J=6.7 Hz, 1H, O—CH$_{2b}$), 3.0-2.5 (m, 8H, N—CH$_2$'s and N—C—CH$_2$a's), 1.57 (m, 2 H, N—C—CH$_2$b's); $^{13}$C NMR (75.5 MHz, DMSO-d6) 176.2, 143.3, 134.6, 134.4, 132.3, 129.0, 124.6, 118.4, 117.6, 114.2, 112.0, 104.0, 97.4, 71.4, 66.3, 58.7, 58.0, 57.8, 50.7, 49.6, 28.5; HRMS, m/e 418.2015 (C$_{24}$H$_{26}$N$_4$O$_3$ requires 418.2005); Anal. Calcd for C$_{24}$H$_{26}$N$_4$O$_3$: C, 68.88; H, 6.26; N, 13.39. Found: C, 68.60; H, 6.19; N, 13.39.

The following compounds can also be synthesized using variations on the Examples described above:

7H-1,4-Dioxino(2,3-e)indole-8-carboxylic acid 2,3,8,9-tetrahydro-2-((4-oxo-1-phenyl-1,3,8-triazaspiro(4.5)dec-8-yl)methyl)-, methyl ester, XIa';

1,3,8-Triazaspiro(4.5)decan-4-one, 8-((2,3-dihydro-8-(hydroxymethyl)-7H-1,4-dioxino(2,3-e)indol-2-yl)methyl)-1-phenyl-, XII;

7H-1,4-Dioxino(2,3-e)indole-8-carboxylic acid, 2,3-dihydro-2-((4-oxo-1-phenyl-1,3,8-triazaspiro(4.5)dec-8-yl)methyl)-7-(2-propenyl)-, methyl ester, XIn;

7H-1,4-Dioxino(2,3-e)indole-8-carboxylic acid, 2,3-dihydro-2-((4-oxo-1-phenyl-3-(2-propenyl)-1,3,8-triazaspiro(4.5)dec-8-yl)methyl)-7-(2-propenyl)-, methyl ester, XIo; and 7H-1,4-Dioxino(2,3-e)indole-8-carboxylic acid, 2,3-dihydro-2-((4-oxo-1-phenyl-3-(2-propenyl)-1,3,8-triazaspiro(4.5)dec-8-yl)methyl)-, methyl ester, XIp.

Formula I Structures

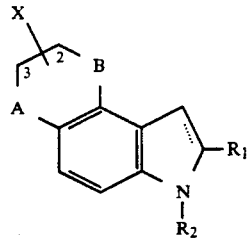

| Compound | X | $R_1$ | $R_2$ | A | B |
|---|---|---|---|---|---|
| XI a | ![structure with (2)N-piperidine-spiro-C(O)NH-N(Ph)] | —$CO_2CH_3$ | H | 0 | 0 |
| a' | ![same structure] | —$CO_2CH_3$(racemate) | | | |
| a" | ![structure with (3)N-piperidine-spiro] | —$CO_2CH_3$ | H | 0 | 0 |
| b | ![structure with (2)N-piperidine-spiro] | —$CO_2CH_3$ | H | 0 | 0 |
| c | " | —$CO_2H$ | H | 0 | 0 |
| d | " | —CN | H | 0 | 0 |
| e | " | —$CO_2C_4H_9$ | H | 0 | 0 |
| f | " | —$CO_2CH_2$—Ph | H | 0 | 0 |
| l | " | —$CH_2OH$ | H | 0 | 0 |
| m | " | H | H | 0 | 0 |
| n | " | —$CO_2CH_3$ | —$CH_2$—CH=$CH_2$ | 0 | 0 |
| o | ![structure with N-allyl] | " | " | 0 | 0 |
| p | " | " | H | 0 | 0 |
| g | ![structure with (2)N-piperidine-benzimidazolone] | " | H | 0 | 0 |

Formula I Structures
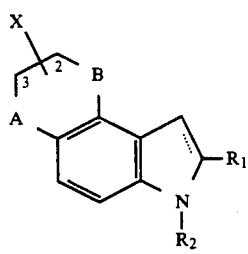
| Compound | X | R₁ | R₂ | A | B |
|---|---|---|---|---|---|
| h | (2)—N(piperidine-4-CO₂C₂H₅) | " | H | 0 | 0 |
| i | (2)—N(piperidine with 4-CONH₂ and 4-NHPh) | " | H | 0 | 0 |
| j | (2)—NH—CH₂CH₂CH₂—Ph | " | H | 0 | 0 |
| k | " | | CH₃C(O)NH—CH₂CH₂CH₂—Ph | H | 0 | 0 |
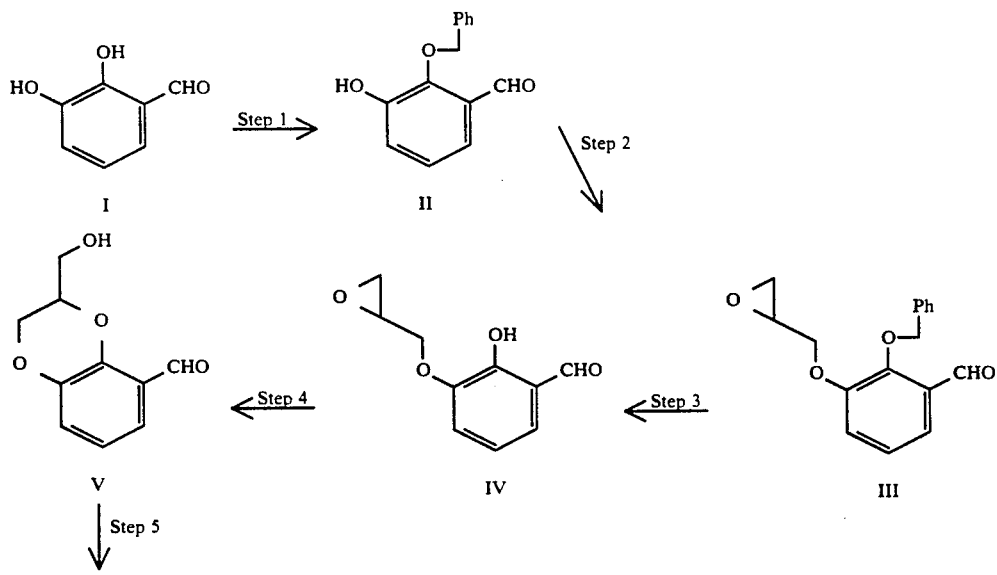
CHART I

CHART I
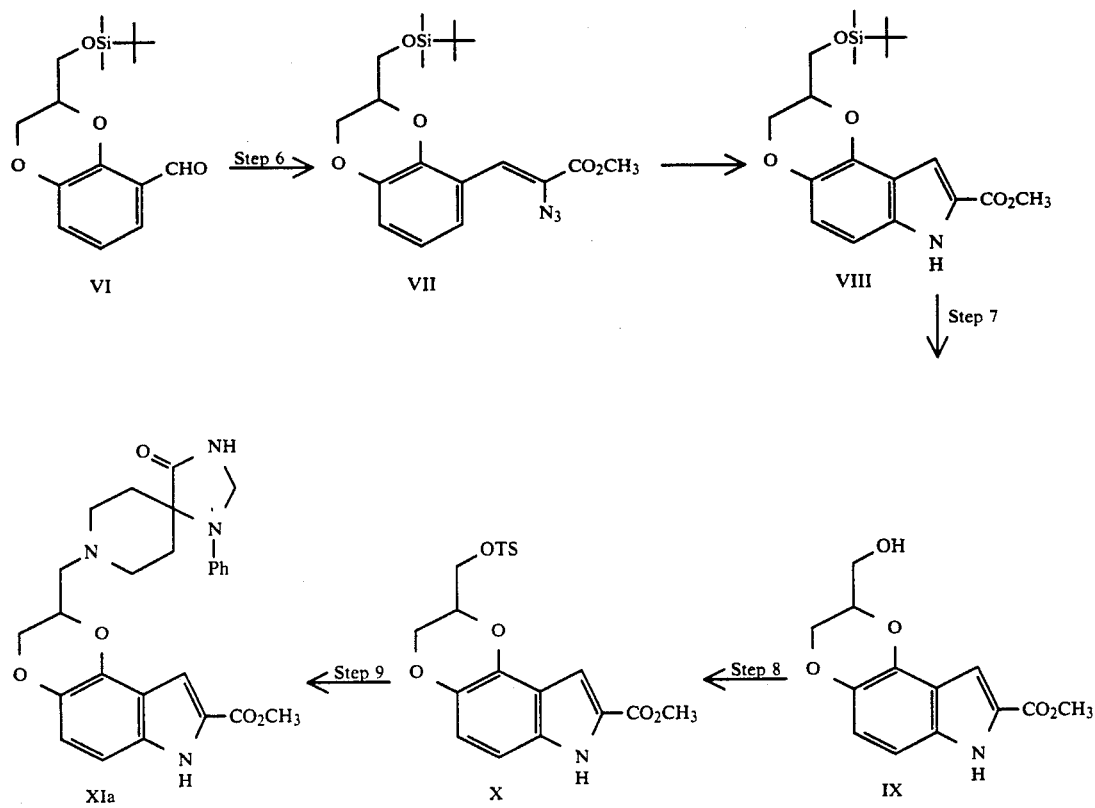
CHART II
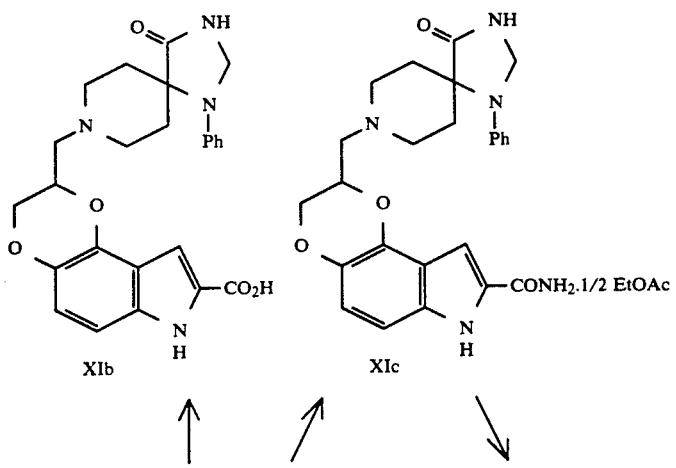

CHART II
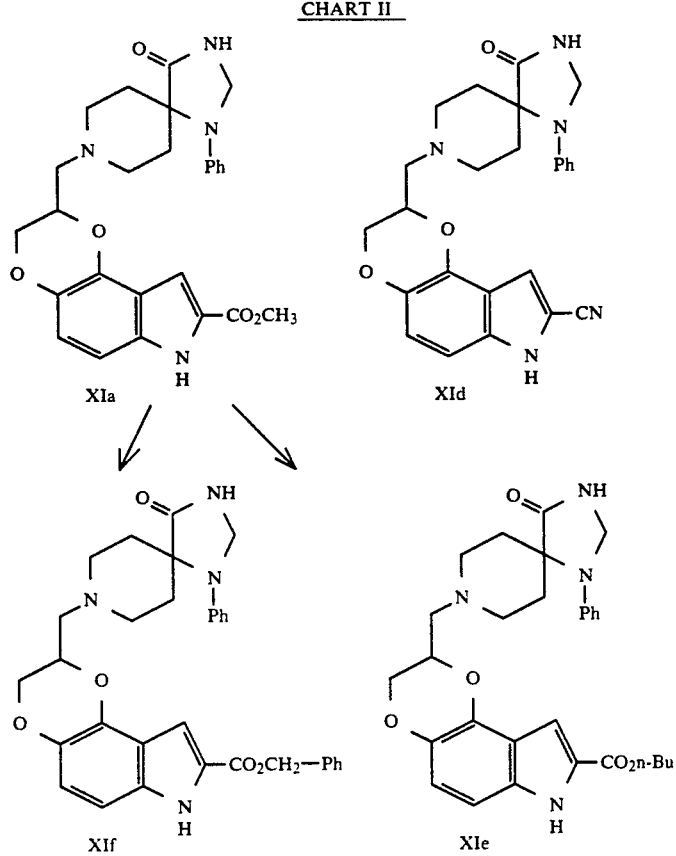
CHART III
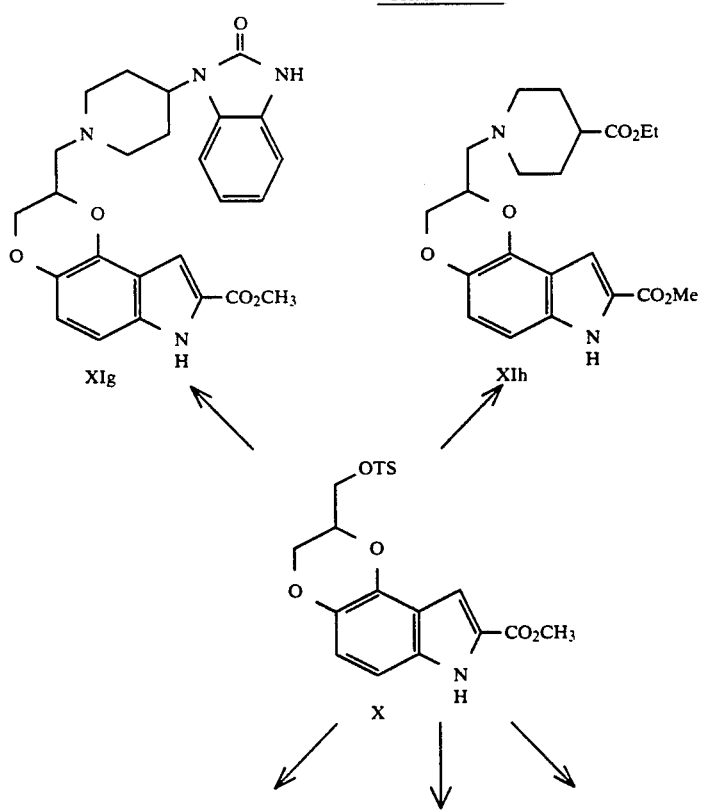

-continued
CHART III

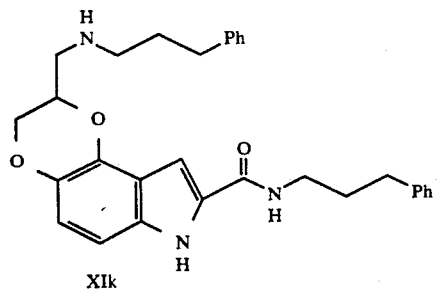 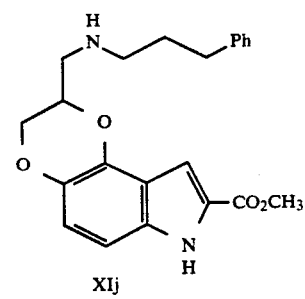 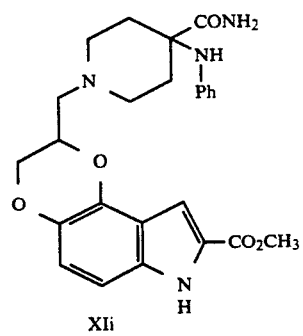

CHART IV

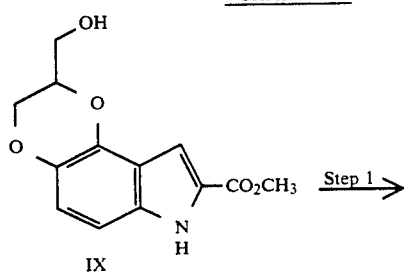

-continued
CHART IV

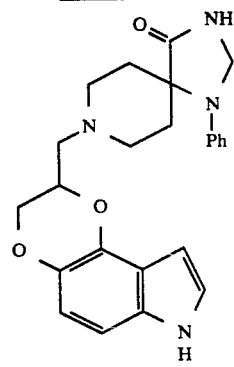

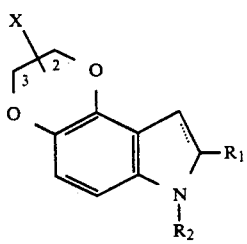

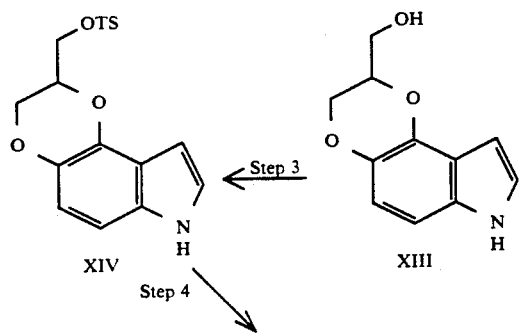

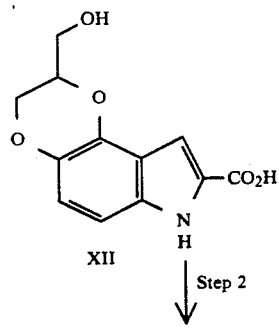

We claim:
1. A compound having the structural formula:

I or pharmaceutically acceptable salts thereof wherein;
$R_1$ is hydrogen,
$C_1$-$C_6$ alkyl, $C_2$-$C_8$ alkenyl, $C_2$-$C_8$ alkynyl,
—$CO_2R_2$,
—$CONHR_2$,
—CN,
halogen,
—CHO,
—$(CH_2)_m$—$OR_2$,
—$(CH_2)_m$—Ar, or
—$SO_2R_2$;
$R_2$ is hydrogen,
$C_1$-$C_6$ alkyl, $C_2$-$C_8$ alkenyl, $C_2$-$C_8$ alkynyl,
—$(CH_2)_m(C_3$-$C_8)$ cycloalkyl or cycloalkenyl, or
—$(CH_2)_m$—Ar where Ar is phenyl optionally substituted with —OH, —O($C_1$-$C_6$ alkyl), halogen, —CH, —CHO, —$(CH_2)_m$—Ph, —$NO_2$, —SH, —S($C_1$-$C_6$ alkyl) or —$NH_2$, —NH($C_1$-$C_6$ alkyl) and m is 0 to 6; and
X is a)

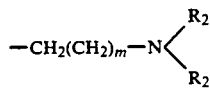

except that one $R_2$ must be a hydrogen or a $C_1$-$CC_6$ alkyl, b)

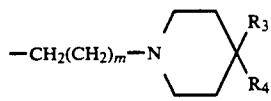

where $R_3$ is hydrogen, —$CO_2R_2$, —$CONHR_2$, —CN, —$NHR_2$, —CHO, —$(CH_2)_m$—Ar, —$NR_2Ar$ or

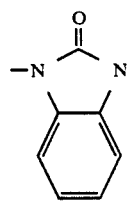

and
$R_4$ is hydrogen, $C_1$-$C_6$ alkyl, $C_2$-$C_8$ alkenyl, $C_2$-$C_8$ alkynyl, —$(CH_2)_m$—$(C_3$-$C_8)$ cycloalkyl or cycloalkenyl, —$(CH_2)_m$—Ar, —$CO_2R_2$, —$CONHR_2$, —CN or —CHO; or c)

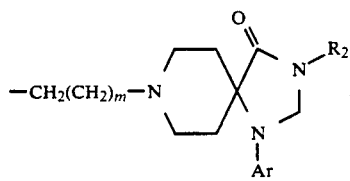

2. The compound of claim 1 wherein $R_2$ is hydrogen.
3. The compound of claim 1 wherein $R_1$ is —$CO_2R_2$.
4. The compound of claim 1 wherein X is

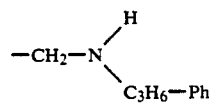

5. The compound of claim 1 wherein X is

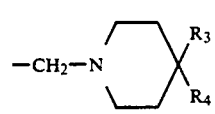

where
$R_3$ is

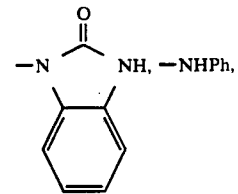

or —$CO_2C_2H_5$ and
$R_4$ is hydrogen or —$CONH_2$.
6. The compound of claim 1 wherein X is

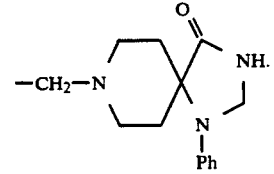

7. A method for treating central nervous system and cardiovascular system disorders related to $5HT_{1A}$ neuronal activity or dopamine receptor activity comprising:
administering to a patient in need thereof a therapeutically effective amount of a compound of Formula I

I or pharmaceutically acceptable salts thereof wherein;
$R_1$ is hydrogen,
$C_1$-$C_6$ alkyl, $C_2$-$C_8$ alkenyl, $C_2$-$C_8$ alkynyl,
—$CO_2R_2$,
—$CONHR_2$,
—CN,
halogen,
—CHO,
—$(CH_2)_m$—$OR_2$,
—$(CH_2)_m$—Ar, or
—$SO_2R_2$;
$R_2$ is hydrogen,
$C_1$-$C_6$ alkyl, $C_2$-$C_8$ alkenyl, $C_2$-$C_8$ alkynyl,
—$(CH_2)_m(C_3$-$C_8)$ cycloalkyl or cycloalkenyl, or
—$(CH_2)_m$—Ar where Ar is phenyl optionally substituted with —OH, —$O(C_1$-$C_6$ alkyl), halogen, —CH, —CHO, —$(CH_2)_m$—Ph, —$NO_2$, —SH, —$S(C_1$-$C_6$ alkyl) or —$NH_2$, —$NH(C_1$-$C_6$ alkyl) and m is 0 to 6; and X is
a)

—$CH_2(CH_2)_m$—N$\begin{smallmatrix}R_2\\R_2\end{smallmatrix}$ except that one R₂ must be a hydrogen or a C₁-CC₆ alkyl, b)

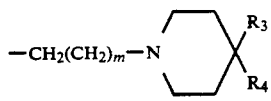

where R₃ is hydrogen, —CO₂R₂, —CONHR₂,

—CN, —NHR₂, —CHO, —(CH₂)ₘ—Ar,

—NR₂Ar or

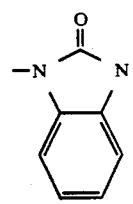

and R₄ is hydrogen, C₁-C₆ alkyl, C₂-C₈ alkenyl, C₂-C₈ alkynyl, —(CH₂)ₘ—(C₃-C₈) cycloalkyl or cycloalkenyl, —(CH₂)ₘ—Ar, —CO₂R₂, —CONHR₂, —CN or —CHO; or c)

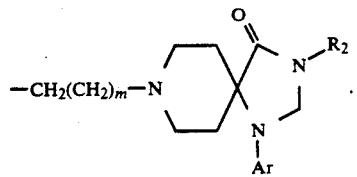

8. The method of claim 7 where said compound of Formula I is administered in an amount of from about 1-2000 mg orally or from about 0.1 to 100 mg parentally.

* * * * *